(12) United States Patent
Wang et al.

(10) Patent No.: US 8,702,758 B2
(45) Date of Patent: Apr. 22, 2014

(54) FLEXIBLE SPINE FIXING STRUCTURE

(75) Inventors: Jaw-Lin Wang, Taipei (TW); Dar-ming Lai, Taipei (TW); Shan-Chang Chueh, Taipei (TW); Chih-Ming Wu, Hsinchu (TW); Shian-Yih Wang, Taipei (TW)

(73) Assignee: Industrial Technology Research Institute, Hsinchu (TW)

( * ) Notice: Subject to any disclaimer, the term of this patent is extended or adjusted under 35 U.S.C. 154(b) by 52 days.

(21) Appl. No.: 13/309,943

(22) Filed: Dec. 2, 2011

(65) Prior Publication Data

US 2012/0078305 A1    Mar. 29, 2012

Related U.S. Application Data

(63) Continuation-in-part of application No. 12/860,066, filed on Aug. 20, 2010, now Pat. No. 8,496,688.

(30) Foreign Application Priority Data

Dec. 31, 2009   (TW) ................................ 98146265 A

(51) Int. Cl.
  *A61B 17/70*   (2006.01)
(52) U.S. Cl.
  USPC .......................................... 606/257; 606/278
(58) Field of Classification Search
  USPC ................................................. 606/246–279
  See application file for complete search history.

(56) References Cited

U.S. PATENT DOCUMENTS

| | | | |
|---|---|---|---|
| 5,470,333 A | 11/1995 | Ray | |
| 5,486,176 A | 1/1996 | Hildebrand et al. | |
| 5,531,746 A | 7/1996 | Errico et al. | |
| 5,545,164 A | 8/1996 | Howland | |
| 5,558,674 A | 9/1996 | Heggeness et al. | |
| 6,283,967 B1* | 9/2001 | Troxell et al. | 606/252 |
| 6,524,315 B1 | 2/2003 | Selvitelli et al. | |
| 6,547,790 B2 | 4/2003 | Harkey, III et al. | |
| 6,902,565 B2 | 6/2005 | Berger et al. | |
| 7,294,129 B2 | 11/2007 | Hawkins et al. | |
| 2003/0191470 A1* | 10/2003 | Ritland | 606/61 |
| 2005/0119657 A1 | 6/2005 | Goldsmith | |
| 2005/0228378 A1* | 10/2005 | Kalfas et al. | 606/61 |
| 2006/0129239 A1 | 6/2006 | Kwak | |
| 2006/0149230 A1 | 7/2006 | Kwak et al. | |

(Continued)

OTHER PUBLICATIONS

TW Office Action (Dated Oct. 16, 2012).

(Continued)

*Primary Examiner* — Mary Hoffman
*Assistant Examiner* — Michelle C Eckman
(74) *Attorney, Agent, or Firm* — McClure, Qualey & Rodak, LLP

(57) ABSTRACT

A flexible spine fixing structure includes a first flexible element and a second flexible element. The first flexible element includes a first flexible part, a first fixing part and a second fixing part. The first fixing part and the second fixing part are respectively connected to two ends of the first flexible part and used for fixing to a first vertebra, and the first flexible part includes a first through hole and a second through hole. The second flexible element includes a second flexible part, a third fixing part and a fourth fixing part. The third fixing part and the fourth fixing part are respectively connected to two ends of the second flexible part and used for fixing to a second vertebra. The second flexible part is disposed by penetrating through the first through hole and the second through hole.

13 Claims, 13 Drawing Sheets

(56) References Cited

U.S. PATENT DOCUMENTS

| | | |
|---|---|---|
| 2006/0149239 A1 | 7/2006 | Winslow et al. |
| 2006/0149254 A1 | 7/2006 | Lauryssen et al. |
| 2006/0149272 A1 | 7/2006 | Winslow et al. |
| 2006/0149289 A1 | 7/2006 | Winslow et al. |
| 2006/0149373 A1 | 7/2006 | Winslow et al. |
| 2006/0149374 A1 | 7/2006 | Winslow et al. |
| 2006/0241597 A1 | 10/2006 | Mitchell et al. |
| 2006/0247632 A1 | 11/2006 | Winslow et al. |
| 2006/0247633 A1 | 11/2006 | Winslow et al. |
| 2006/0247650 A1 | 11/2006 | Yerby et al. |
| 2006/0264939 A1 | 11/2006 | Zucherman et al. |
| 2006/0271046 A1 | 11/2006 | Kwak et al. |
| 2006/0276794 A1 | 12/2006 | Stern |
| 2006/0282077 A1 | 12/2006 | Labrom et al. |
| 2007/0016196 A1 | 1/2007 | Winslow et al. |
| 2007/0016218 A1 | 1/2007 | Winslow et al. |
| 2007/0123863 A1 | 5/2007 | Winslow et al. |
| 2007/0123872 A1 | 5/2007 | Brockmeyer et al. |
| 2007/0162001 A1 | 7/2007 | Chin et al. |
| 2007/0233088 A1 | 10/2007 | Edmond |
| 2007/0244483 A9 | 10/2007 | Winslow et al. |
| 2007/0282339 A1* | 12/2007 | Schwab .................. 606/61 |
| 2008/0033433 A1 | 2/2008 | Implicito |
| 2008/0058818 A1* | 3/2008 | Schwab .................. 606/73 |
| 2008/0177323 A1* | 7/2008 | Null et al. .............. 606/267 |
| 2008/0269804 A1 | 10/2008 | Holt |
| 2009/0163953 A1* | 6/2009 | Biedermann et al. ......... 606/254 |
| 2009/0259256 A1* | 10/2009 | Miller .................. 606/250 |
| 2009/0264931 A1* | 10/2009 | Miller et al. ............ 606/251 |
| 2011/0152932 A1 | 6/2011 | Wang et al. |
| 2012/0016417 A1 | 1/2012 | Druma |

OTHER PUBLICATIONS

Non-Final Office Action mailed Apr. 26, 2012 for U.S. Appl. No. 12/860,066 filed Aug. 20, 2010.

* cited by examiner

FLEXIBLE SPINE FIXING STRUCTURE

This is a continuation-in-part application of U.S. application Ser. No. 12/860,066, filed Aug. 20, 2010, which claims the benefit of Taiwan application Serial No. 98146265, filed Dec. 31, 2009, and the disclosure of which is incorporated by reference herein in its entirety.

BACKGROUND

1. Technical Field

The disclosure relates in general to a flexible spine fixing structure, and more particularly to a flexible spine fixing structure for fixing to two or more vertebras.

2. Description of the Related Art

Normally, there are various methods to fix vertebras of a spine. One of them is to fix a number of vertebras by transverse fixing plates and then fix the fixing plates together by a longitudinal rigid structure. Another fixing structure is composed of two vertebral plates and screws. Each of the vertebral plates has a hole of a fixed angle, and the vertebral screws penetrate two vertebras through the holes to fix the two vertebras.

However, no matter which method is used, the fixed spine loses its mobility and thus the patient receiving the surgery cannot move his/her spine, such as to bend forwards or backwards. Besides, when the fixed vertebras cannot move for a long time, they will gradually fuse into a single vertebra to lose mobility forever and result in fast degeneration of neighboring vertebras.

SUMMARY

The disclosure is directed to a flexible spine fixing structure. Through its flexibility, the fixed vertebras may still move, thereby providing the spine of the patient with higher mobility, reducing discomfort of the patient after the surgery and avoiding spine degeneration.

According to an embodiment of the present disclosure, a flexible spine fixing structure for fixing to a first vertebra and a second vertebra is provided. The flexible spine fixing structure comprises a first joint element, a second joint element, a first flexible element and a second flexible element. The first joint element comprises a protrusion and a flange disposed on the protrusion. The second joint element comprises a receiving cavity and a block portion disposed in the receiving cavity, wherein an inner diameter of the block portion is smaller than an outer diameter of the flange, and the first joint element is flexibly connected to the second joint element through the flange being movably disposed within the receiving cavity. The first flexible element passes through the first joint element for fixing to the first vertebra. The second flexible element passes through the second joint element for fixing to the second vertebra.

Figure 1:
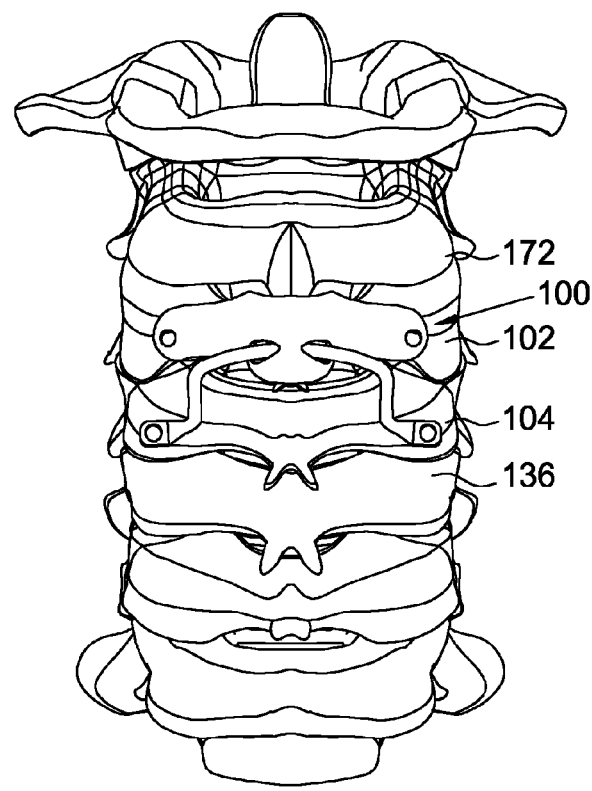
FIG. 1 is a schematic diagram of the flexible spine fixing structure configured on vertebras according to a first embodiment of the disclosure.

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

DETAILED DESCRIPTION

First Embodiment

Referring to FIG. 1, a schematic diagram of the flexible spine fixing structure configured on vertebras according to a first embodiment of the disclosure is shown. The flexible spine fixing structure 100 is for fixing to a first vertebra 102 and a second vertebra 104, which are adjacent to each other. The first vertebra 102 and the second vertebra 104 are not limited to specific vertebras and can be any two vertebras of a spine, such as two vertebras of a cervical spine, a thoracic spine or a lumbar spine.

Figure 2:
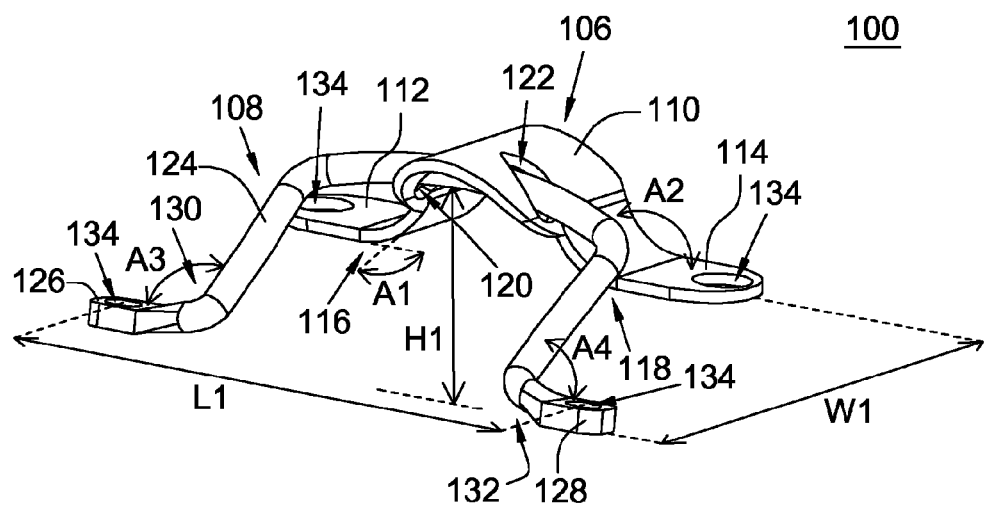
FIG. 2 is a schematic diagram of the flexible spine fixing structure of FIG. 1.

Referring to FIG. 2, a schematic diagram of the flexible spine fixing structure of FIG. 1 is shown. The flexible spine fixing structure 100 includes a first flexible element 106 and a second flexible element 108. The first flexible element 106 includes a first flexible part 110, a first fixing part 112 and a second fixing part 114. The first fixing part 112 and the second fixing part 114 are connected to a first end 116 and a second end 118 of the first flexible part 110 respectively and are used for fixing to the first vertebra 102. The first flexible part 110 has a first through hole 120 and a second through hole 122.

Each of the first fixing part 112, the second fixing part 114, the third fixing part 126 and the fourth fixing part 128 has a through hole 134. A number of fixing elements, such as screws (not shown in the figure) are used to penetrate through the through holes to lock the first fixing part 112, the second fixing part 114, the third fixing part 126 and the fourth fixing part 128 onto the first vertebra 102 and the second vertebra 104.

In another example, the first fixing part 112, the second fixing part 114, the third fixing part 126 and the fourth fixing part 128 each can also be a board having a through hole, and are, for example, fixed to the first flexible part 110 and the second flexible part 124 by welding.

The second flexible element 108 includes a second flexible part 124, a third fixing part 126 and a fourth fixing part 128. The third fixing part 126 and the fourth fixing part 128 are connected to a third end 130 and a fourth end 132 of the second flexible part 124 respectively and are used for fixing to the second vertebra 104. The second flexible part 124 penetrates the first through hole 120 and the second through hole 122.

The second flexible part 124 is directly connected to the first flexible part 110 such that the whole flexible spine fixing structure 100 has flexibility. That is, after the flexible spine fixing structure 100 is fixed to the vertebras, the fixed vertebras can still move. Therefore, the patient can still bend his/her body forwards or backwards or turn his/her body left or right to have a higher mobility and lower discomfort after surgery, and spine degeneration can be avoided.

The first flexible part 110 and the second flexible part 124 of the embodiment can achieve the effect of flexibility by way of selecting proper appearance, materials, a cross-sectional shape or other parameters. In the following description, the structure of the first flexible part 110 and the second flexible part 124 is illustrated in detail.

Each of the first flexible part 110 and the second flexible part 124 can have a shape of an arc. An included angle A1 between the first fixing part 112 and the first flexible part 110, an included angle A2 between the second fixing part 114 and the first flexible part 110, an included angle A3 between the third fixing part 126 and the second flexible part 124 and an included angle A4 between the fourth fixing part 128 and the second flexible part 124 are all obtuse angles. Preferably but not limited thereto, the obtuse angle is between 120 and 150 degrees. By doing so, the first flexible part 110 and the second flexible part 124 can have flexibility such that the two fixed vertebras can still move.

Besides, each of the first flexible part 110 and the second flexible part 124 can have a cross-sectional shape of a rectangle, a circle or an ellipse and have an appearance of being flat or long and thin in order that the first flexible part 110 and the second flexible part 124 can have the flexibility.

The first flexible part 110 and the second flexible part 124 can be made of metal, polymer, flexible materials, elastic materials or combination thereof. For example, the metal may be realized by bio-compatible metal, stainless steel, memory alloy or a metal containing titanium such as pure titanium or titanium alloy. The polymer may be realized by polyether ether ketone (PEEK), polytetrafluoroethylene (PTFE, that is Teflon) or polyethylene terephthalate (PET).

The first flexible element 106 can be manufactured by way of integrally formed in one piece, such as injection molding or plate bending. The second flexible element 108 is made by the same way as the first flexible element 106, and thus any detail is unnecessary to be given here.

Furthermore, metal wires can be embedded in the above flexible parts. For example, in another example, if the first flexible part 110 is made of polytetrafluoroethylene having soft texture, a metal wire (not shown in the figure) can be embedded in the first flexible part 110 to increase rigidity, elasticity and flexibility of the first flexible part 110. Of course, it the second flexible part 124 is also made of soft-texture material, the same processing can be done to the second flexible part 124.

Moreover, the height H1 of the fixing part relative to a top of the flexible part, the interval L1 between the through hole 134 of the third fixing part 126 and the through hole 134 of the fourth fixing part 128 and the interval W1 between the through hole 134 of the fourth fixing part 128 and the through hole 134 of the second fixing part 114 can be suitably designed such that the flexible spine fixing structure 100 does not interfere with the vertebras. For example, according to a scale of a normal vertebra, the height H1 is between 0 mm and 25 mm, the interval L1 is between 30 mm and 60 mm, and the interval W1 is between 10 mm and 25 mm.

The height H1 can be used to prevent the flexible spine fixing structure 100 from interfering with the spinous process or spinal cord. Although the height H1 is exemplified to be a distance of the fourth fixing part 128 from the second flexible part 124, the height H1 can also be a distance of the third fixing part 126 from the second flexible part 124.

The scale ranges of the above height H1, intervals L1 and W1 are not used to limit the embodiment, the actual scale can be designed based on a scale of the actual spine under surgery. That is, the flexible spine fixing structure 100 of the embodiment can be manufactured to fit the spines having different scales.

Second Embodiment

Figure 3:
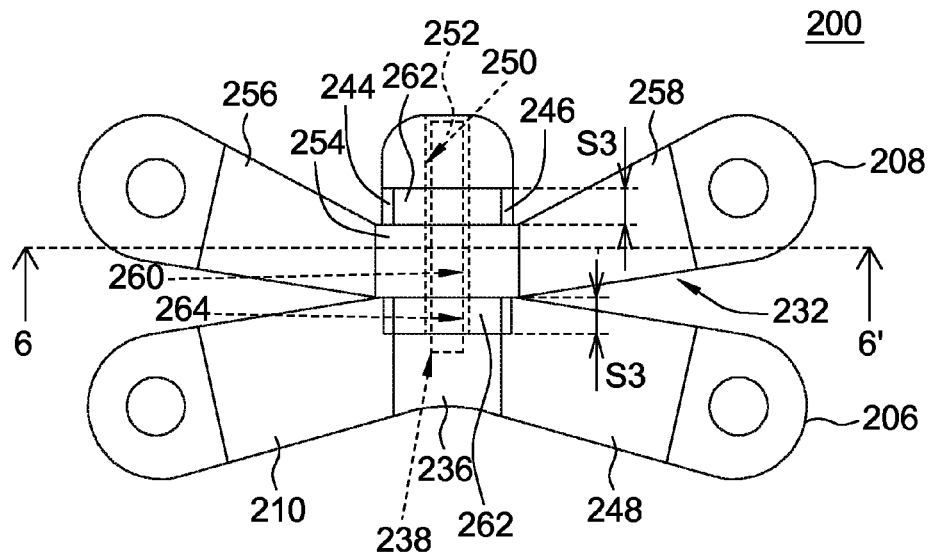
FIG. 3 is a schematic diagram of the flexible spine fixing structure according to the second embodiment of the disclosure.

Referring to FIG. 3, a schematic diagram of the flexible spine fixing structure according to the second embodiment of the disclosure is shown. The flexible spine fixing structure 200 is for fixing to the first vertebra 102 and the second vertebra 104.

The flexible spine fixing structure 200 includes a first flexible element 206, a second flexible element 208, a shaft 252 and two spacers 262. The shaft 252 is disposed by penetrating the first flexible element 206, the second flexible element 208 and the spacers 262 to prevent the first flexible element 206, second flexible element 208 and spacers 262 departing from each other.

The shaft 252 is a flexible rod and can be made of bio-compatible elastic rope, polymer, metal or other flexible or elastic material or combination thereof.

The first flexible element 206 and the second flexible element 208 can be made of metal, polymer, flexible materials, elastic materials or combination thereof. For example, the metal may be realized by bio-compatible metal, stainless steel, memory alloy or a metal containing titanium such as pure titanium or titanium alloy. The polymer may be realized by polyether ether ketone (PEEK), polytetrafluoroethylene (PTFE, that is Teflon) or polyethylene terephthalate (PET).

Owing that the first flexible element 206, the second flexible element 208, the shaft 252 and the two spacers 262 have flexibility, the whole spine fixing structure 200 has flexibility. To give a further description, when the flexible spine fixing structure 200 is fixed to the vertebras, the fixed vertebras can still move, and thus the patient can still bend his/her body forwards or backwards or turn his/her body left or right to have a higher mobility and lower discomfort after surgery and the spine degeneration can be avoided.

In the following description, the structure of the flexible spine fixing structure 200 is illustrated in detail.

Figure 4:
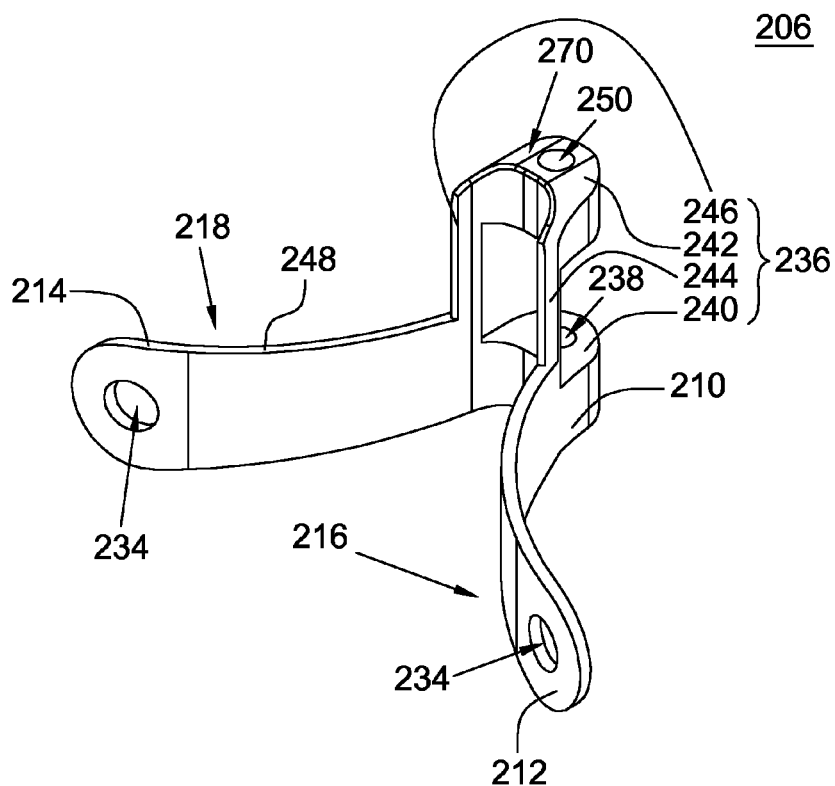
FIG. 4 is a schematic diagram of the first flexible element of FIG. 3.

FIG. 4 is a schematic diagram of the first flexible element 206 of FIG. 3. Referring to FIGS. 3 and 4 at the same time, the first flexible element 206 includes a first connecting part 236, a first flexible part 210, a second flexible part 248, a first fixing part 212 and a second fixing part 214. One end of the first flexible part 210 and one end of the second flexible part 248 are respective connected to two opposite ends of the first connecting part 236. The first fixing part 212 and the second fixing part 214 are connected to a first end 216 of the first flexible part 210 and a second end 218 of the second flexible part 248 respectively and are used for fixing to the second vertebra 104 of FIG. 1.

To give a further description, each of the first fixing part 212 and the second fixing part 214 has a through hole 234. These through holes 234 are for a number of fixing elements, such as screws (not shown in the figure) to penetrate through so as to lock the first fixing part 212 and the second fixing part 214 onto the second vertebra 104.

The first flexible element 206 can be manufactured by integrally formed in one piece, such as injection molding or plate bending.

In another example, the first flexible part 210, the second flexible part 248, the first fixing part 212 and the second fixing part 214 can be manufactured individually. For example, the first fixing part 212 and the second fixing part 214 each can also be a board having a through hole (not shown in the figure), and are fixed to the first flexible part 210 and the second flexible part 248 by welding.

The first connecting part has an indent 238, and the shaft 252 can be disposed in the indent 238. The indent 238 can be a blind hole or a through hole. In the embodiment, the indent 238 is exemplified by a blind hole for illustration.

As shown in FIG. 4, the first connecting part 236 includes a first connecting piece 240, a second connecting piece 242, a first beam 244 and a second beam 246. The first beam 244 and the second beam 246 are disposed in parallel to each other and connected to the first connecting piece 240 and the second connecting piece 242. The indent 238, the first flexible part 210 and the second flexible part 248 are formed on the first connecting piece 240. The second connecting piece 242 has a second through hole 250 and one end of the shaft 252 penetrates the second through hole 250 to be disposed in the indent 238.

Besides, the side surface 270 of the second connecting piece 242 can block an adjacent upper vertebra, such as the third vertebra 172 neighboring the first vertebra 102 in FIG. 1. The second connecting piece 242 has an effect of supporting the third vertebra 172, sharing stress for the vertebra 102 and maintaining a height position of the vertebra 102.

Figure 5:
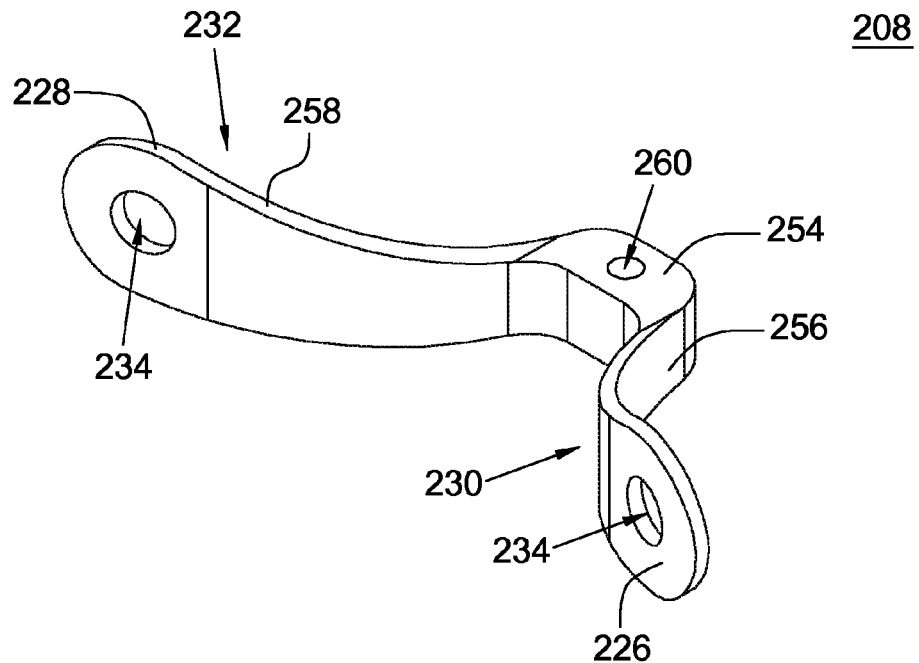
FIG. 5 is a schematic diagram of the second flexible element of FIG. 3.

FIG. 5 is a schematic diagram of the second flexible element 208 of FIG. 3. Referring to FIGS. 3 and 5 at the same time, the second flexible element 208 includes a second connecting part 254, a third flexible part 256, a fourth flexible part 258, a third fixing part 226 and a fourth fixing part 228. One end of the third flexible part 256 and one end of the fourth flexible part 258 are connected to two opposite ends of the second connecting part 254 respectively. The third fixing part 226 and the fourth fixing part 228 are connected to a third end 230 of the third flexible part 256 and a fourth end 232 of the fourth flexible part 258 respectively and used for fixing to the first vertebra 102 of FIG. 1. The second connecting part 254 has a first through hole 260 and the shaft 252 penetrates the first through hole 260.

Each of the third fixing part 226 and the fourth fixing part 228 has a through 234. The through holes 234 are for a number of fixing elements, such as screws (not shown in the figure), to penetrate through so as to lock the third fixing part 226 and the fourth fixing part 228 onto the first vertebra 102.

The second flexible element 208 can be manufactured by integrally formed in one piece, such as injection molding or plate bending.

In another example, the third flexible part 256, the fourth flexible part 258, the third fixing part 226 and the fourth fixing part 228 can be manufactured individually. For example, the third fixing part 226 and the fourth fixing part 228 each can also be a board having a through hole, and can be fixed to the third flexible part 256 and the fourth flexible part 258 by welding.

Figure 6:
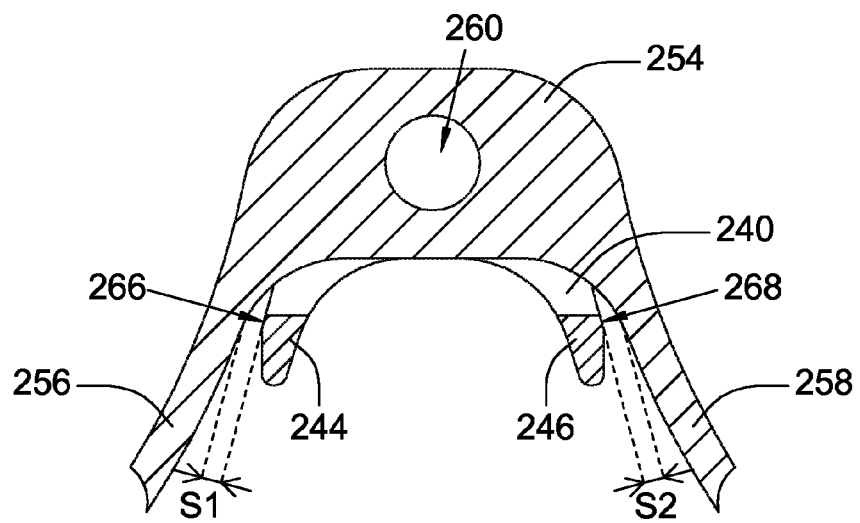
FIG. 6 is a cross-sectional diagram of the flexible spine fixing structure of FIG. 3 along a line 6-6'.

Referring to FIG. 6, a cross-sectional diagram of the flexible spine fixing structure of FIG. 3 along a line 6-6' is shown. The first beam 244 has a first side surface opposite to the third flexible part 256, and the first side surface 266 is separated from the third flexible part 256 by a first interval S1. The second beam 246 has a second side surface 268 opposite to the fourth flexible part 258, and the second side surface 268 is separated from the fourth flexible part 258 by a second interval S2. The first interval S1 and the second interval S2 are used to provide sufficient space for motion of the second flexible element 208 such that the vertebras fixed by the third fixing part 226 and the fourth fixing part 228 can have higher mobility, wherein each of the first interval S1 and the second interval S2 is about 0.4 mm.

Further, the first side surface 266 and the second side surface 268 also have the effect of blocking the second flexible element 208. For example, when the second flexible element 208 turns to contact the first side surface 266, the first side surface 266 blocks the second flexible element 208 from continuing to turn. Therefore, the over-large rotation of the second flexible element 208 can be constrained to avoid spine injury due to unduly exercise.

Figure 7:
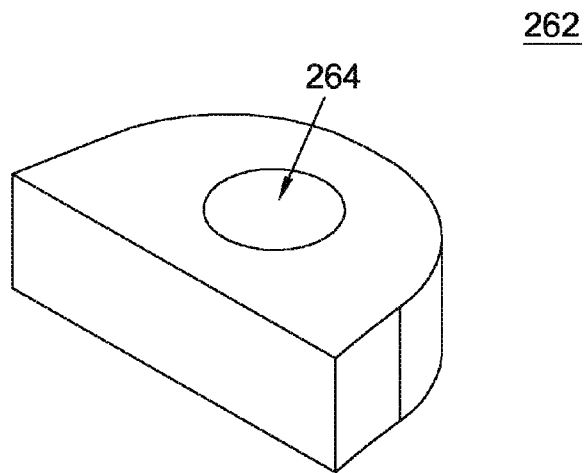
FIG. 7 is a schematic diagram of the spacer of FIG. 3.

FIG. 7 is a schematic diagram of the spacer of FIG. 3. Referring to FIGS. 3 and 7, the first connecting part 236 is separated from the second connecting part 254 by third intervals S3, and two spacers 262 are disposed in the third interval S3. In the embodiment, the two spacers 262 are disposed at two opposite ends of the second connecting part 254 respectively and roughly fill up the gap between the first connecting part 236 and the second connecting part 254, thereby preventing tissues of the human body from being incautiously clapped into the above gap.

The spacers 262 can interfere or cooperate in a lessen or medium extent with the second connecting part 254, the first connecting piece 240 and the second connecting piece 242, which depends on the real situation in an actual application and is not limited in the embodiment.

Each of the spacer 262 has a third through hole 264. The shaft 252 penetrates the second through hole 250, the third through hole 264 and the first through hole 260 and is disposed in the indent 238, as shown in FIG. 3.

In the embodiment, an outer diameter of the shaft 252 is smaller than inner diameters of the first through hole 260, the second through hole 250 and the third through hole 264, and an outer diameter of the shaft 252 is larger than an inner diameter of the indent 238 such that the shaft 252 can penetrate the first through hole 260, the second through hole 250 and the third through hole 264 to be fixed into the indent 238, as shown in FIG. 3 to prevent the shaft 252 falling off and the first flexible element 206, the second flexible element 208 and the spacers 262 separating from each other.

Owing that the outer diameter of the shaft 252 is smaller than the inner diameters of the first through hole 260, the second through hole 250 and the third through 264, a gap (not shown in the figure) among the shaft 252, the first through hole 260, the second through hole 250 and the third through hole 264 is formed to provide a space for flexible deformation of the first flexible element 206 and the second flexible element 208. Therefore, the second flexible element 208 can move relative to the shaft 252.

Although the outer diameter of the shaft 252 is exemplified to be smaller than the inner diameters of the first through hole 260, the second through hole 250 and the third through hole 264 for illustration in the embodiment, the disclosure is not limited thereto. In another example, the outer diameter of the shaft 252 can be larger than the inner diameter of one of the first through hole 260, the second through hole 250 and the third through hole 264. Under this situation, the inner diameter of the indent 238 can be larger than the outer diameter of the shaft 252.

Although the shaft 252 is exemplified to have flexibility in the embodiment, in another example, the shaft 252 can also be a rigid shaft. If the shaft 252 is a rigid shaft, preferably, the outer diameter of the shaft 252 is smaller than the inner diameters of the first through hole 260, the second through hole 250 and the third through hole 264 such that the shaft 252 and the through holes form a gap. The gap provides a space for flexible deformation of the first flexible element 206 and the second flexible element 208.

The first flexible part 210, the second flexible part 248, the third flexible part 256 and the fourth flexible part 258 can achieve the effect of flexibility by way of selecting proper appearance, materials, a cross-sectional shape or other parameters in the embodiment. In the following description, the structures of the first flexible part 210, the second flexible part 248, the third flexible part 256 and the fourth flexible part 258 are given in detail.

Figure 8:
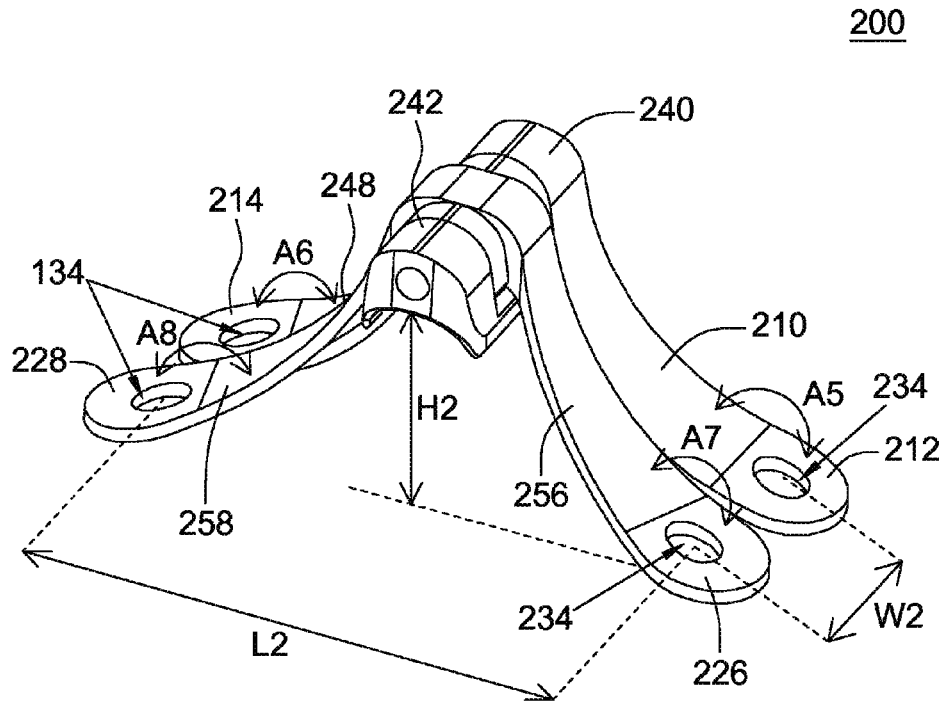
FIG. 8 is a schematic diagram of the scales of the flexible spine fixing structure of FIG. 3.

Referring to FIG. 8, a schematic diagram of the scales of the flexible spine fixing structure of FIG. 3 is shown. Each of the first flexible part 210, the second flexible part 248, the third flexible part 256 and the fourth flexible part 258 has a shape of an arc. An included angle A5 between the first fixing part 212 and the first flexible part 210, an included angle A6 between the second fixing part 214 and the second flexible part 248, an included angle A7 between the third fixing part 226 and the third flexible part 256 and an included angle A8 between the fourth fixing part 228 and the fourth flexible part 258 are all obtuse angles. Preferably but not limited thereto, the obtuse angle is between 120 degrees and 150 degrees. By doing so, the first flexible part 210 and the second flexible part 248 can have flexibility.

Besides, taking the third fixing part 226 as an example, the height H2 of the third fixing part 226 relative to the first connecting piece 240 or the second connecting piece 242, the interval W2 between the through hole of the first fixing part 212 and the through hole of the third fixing part 226 and the interval L2 between the through hole of the third fixing part 226 and the through hole of the fourth fixing part 228 can be suitably designed such that the flexible spine fixing structure 200 does not interfere with the vertebra or contact the spinal cord. For example, according to a scale of a normal vertebra, the height H2 is between 0 mm and 25 mm, the interval L2 is between 30 mm and 40 mm, and the interval W2 is between 10 mm and 15 mm.

Although the height H2 is exemplified to be a distance between the third fixing part 226 and the second connecting piece 242 for illustration, the height H2 may also be a height of any fixing part relative to the first connecting piece 240 or the second connecting piece 242.

Moreover, a distance (not shown in the figure) between the through hole 234 of the second fixing part 214 and the through hole 234 of the fourth fixing part 228 is roughly between 10 mm and 15 mm.

Although the interval W2 is exemplified to be a distance between the through hole of the first fixing part 212 and the through hole of the third fixing part 226 for illustration, the interval W2 can also be a distance between the through hole of the second fixing part 214 and the through hole of the fourth fixing part 228.

Furthermore, in addition to a rectangle, the first flexible part 210, the second flexible part 248, the third flexible part 256 and the fourth flexible part 258 can also have a cross-sectional shape of a circle or an ellipse. In this case, the first flexible part 210, the second flexible part 248, the third flexible part 256 and the fourth flexible part 258 can similarly generate suitable deformation after receiving stress.

Moreover, metal wires can be embedded in the flexible parts. For example, in another example, if the first flexible part 210 is made of polytetrafluoroethylene having soft texture, a metal wire (not shown in the figure) can be embedded in the first flexible part 210 to improve rigidity, elasticity and flexibility of the first flexible part 210. Of course, if the second flexible part 248, the third flexible part 256 or the fourth flexible part 258 has soft texture, the above processing can also be done to these flexible parts.

Third Embodiment

Figure 9:
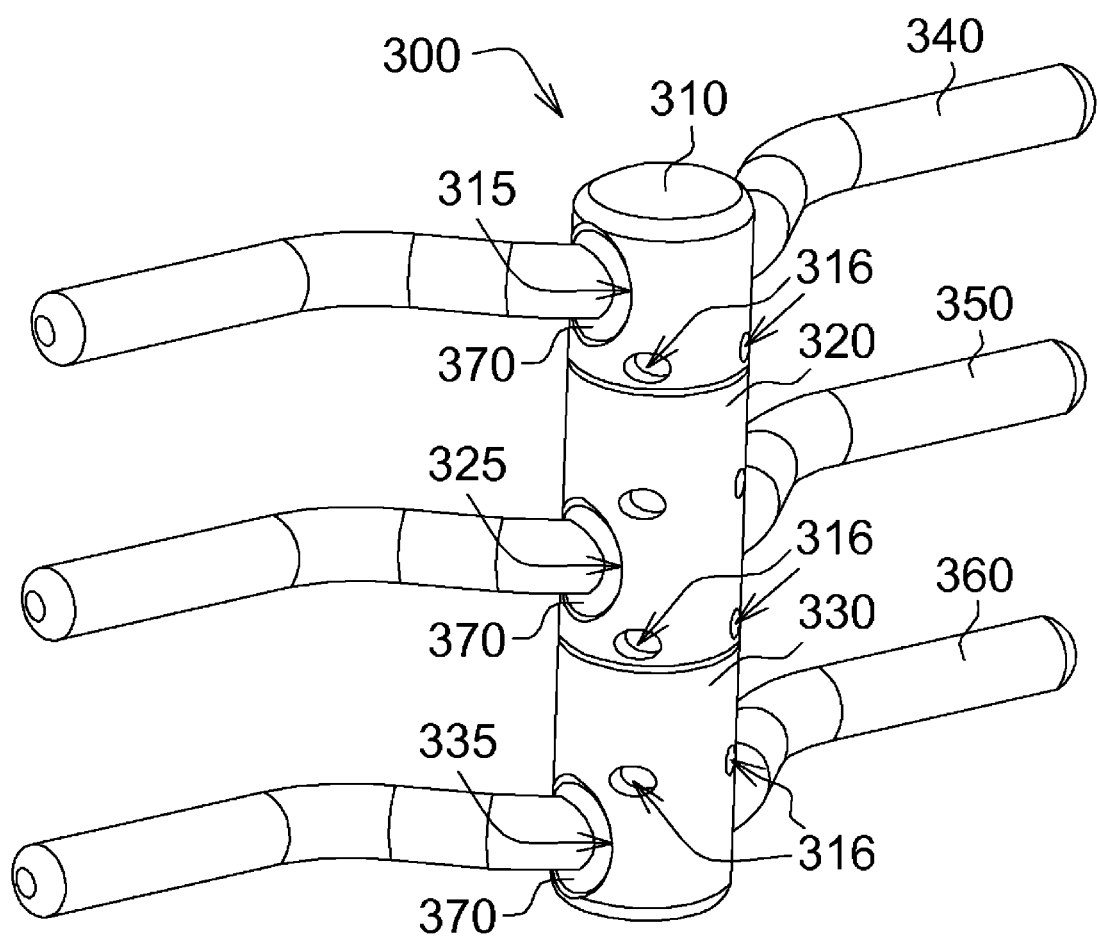
FIG. 9 is a schematic diagram of the flexible spine fixing structure configured on vertebras according to a third embodiment of the disclosure.

Referring to FIG. 9, a schematic diagram of the flexible spine fixing structure configured on vertebras according to a third embodiment of the disclosure is shown. The flexible spine fixing structure 300 is for fixing to a first vertebra 102, a second vertebra 104 and a third vertebra 136, which are adjacent to each other.

The flexible spine fixing structure 300 comprises a first joint element 310, a second joint element 320, a third joint element 330, a first flexible element 340, a second flexible element 350 and a third flexible element 360. The first joint element 310 has a first through hole 315, and the first flexible element 340 passes through the first through hole 315 of the first joint element 310. The second joint element 320 has a second through hole 325, and the second flexible element 350 passes through the second through hole 325 of the second joint element 320. The third joint element 330 has a third through hole 335, and the third flexible element 360 passing through the third through hole 335 of the third joint element 330. The first flexible element 340 is fixed on the first vertebra 102 through a first polyaxial screw or any pedicel fastener (not illustrated), the second flexible element 350 is fixed on the second vertebra 104 through a second polyaxial screw or any pedicel fastener (not illustrated), and the third flexible element 360 is fixed on the third vertebra 136 through a third polyaxial screw or any pedicel fastener (not illustrated). In another embodiment, the flexible spine fixing structure 300 may omit the third joint element 330.

In present embodiment, the first joint element 310 is detachably connected to the second joint element 320, and the second joint element 320 is detachably connected to the third joint element 330. The first joint element 310, the second joint element 320 and the third joint element 330 may be assembled before the flexible spine fixing structure 100 is fixed to the vertebras. In one embodiment, several second joint elements 320 may connect to each other, such that the flexible spine fixing structure 100 is fixed to more than three vertebras.

In one embodiment, the structure of the first flexible element 340, the structure of the second flexible element 350 and the structure of the third flexible element 360 are similar. In addition, the material of the first flexible element 340, the material of the second flexible element 350 and the material of the third flexible element 360 are similar. The material of the first flexible element 340, the second flexible element 350 and the third flexible element 360 are similar to the material of the first flexible part 110. The material of the first flexible element 340, the second flexible element 350 and the third flexible element 360 are different or the same.

The material of the first joint element 310, the second joint element 320 and the third joint element 330 are similar to the material of the first flexible part 110. The material of the first joint element 310, the second joint element 320 and the third joint element 330 are different or the same.

Figure 10A:
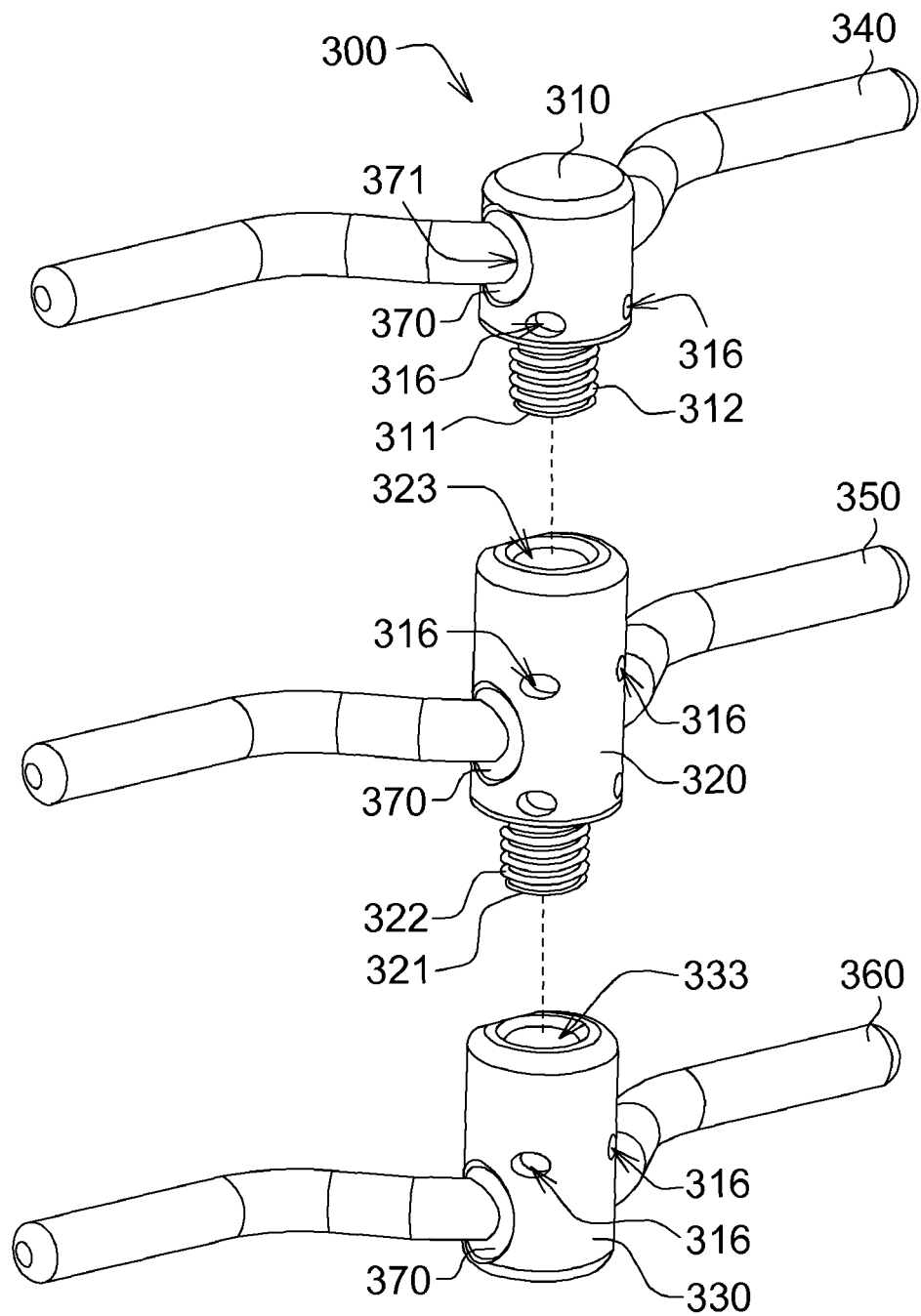
FIG. 10A is a explode view of the flexible spine fixing structure of FIG. 9.

Referring to FIG. 10A, a explode view of the flexible spine fixing structure of FIG. 9 is shown. The first joint element 310 comprises a protrusion 311 and a flange 312 disposed on the protrusion 311, wherein an outer diameter of the flange 312 is larger an outer diameter of the protrusion 311. In present embodiment, the flange 312 of the first joint element 310 is a pin thread which surrounds the protrusion 311. The first joint element 310 is connected to second joint element 320 through the flange 312.

Figure 10B:
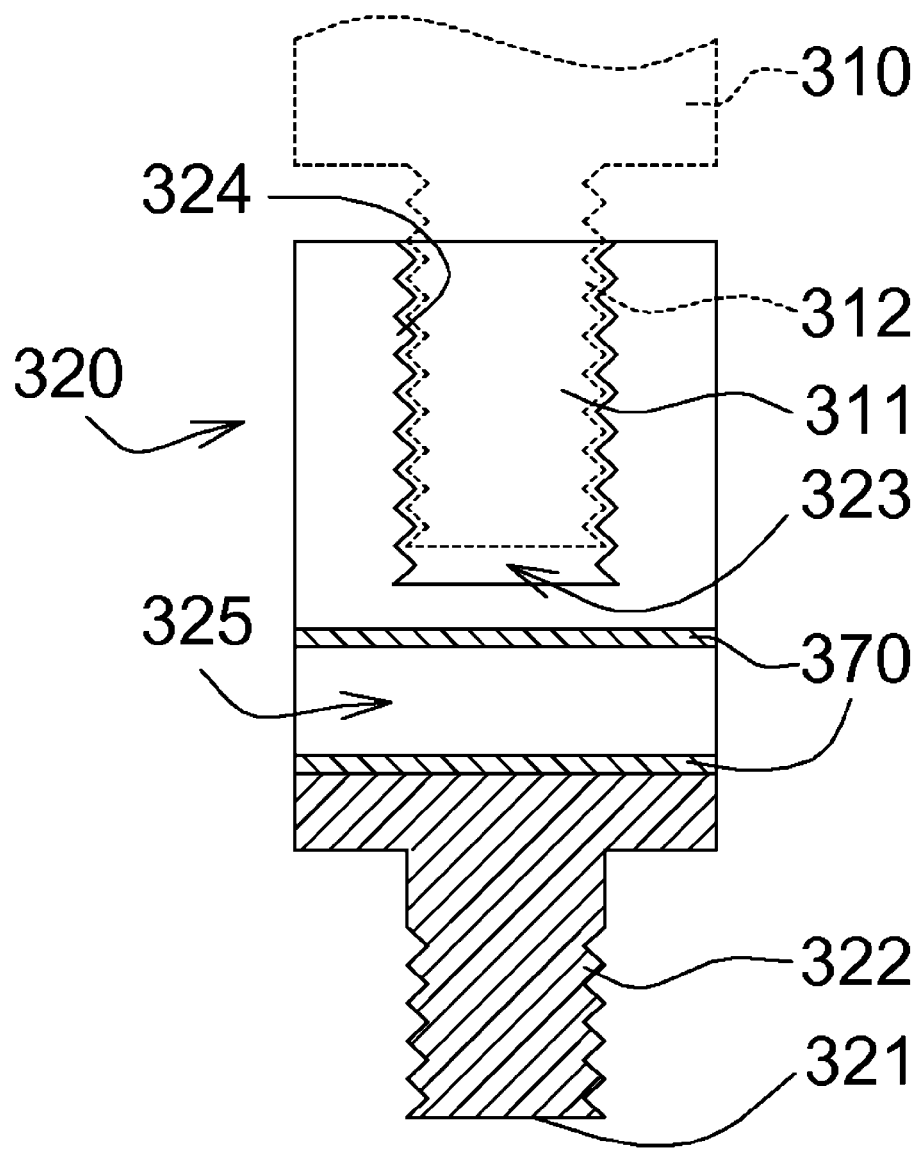
FIG. 10B is a cross-section view of the second joint element of FIG. 10A.

Referring to FIGS. 10A and 10B, and FIG. 10B is a cross-section view of the second joint element of FIG. 10A. The second joint element 320 comprises a receiving cavity 323 and a block portion 324 disposed in the receiving cavity 323, wherein an inner diameter of the block portion 324 is smaller than an outer diameter of the flange 312 of the first joint element 310, and the first joint element 310 is movably connected to the second joint element 320 through the flange 312 being movably disposed within the receiving cavity 323. In present embodiment, the block portion 324 is female thread corresponding to the pin thread (that is the flange 312). A screw clearance is located between the pin thread (that is flange 312) and the female thread (that is the block portion 324), such that the first joint element 310 is movably connected to second joint element 320. In another embodiment, the pin thread (that is flange 312) fine fit the female thread (that is the block portion 324).

In addition, the second joint element 320 further comprises a protrusion 321 and a flange 322 which are similar to the protrusion 311 and the flange 312 respectively. The second joint element 320 is connected to third joint element 330 through the flange 322. Since the second joint element 320 further comprises the protrusion 321 and the flange 322, several second joint elements 320 may connect to each other, such that the flexible spine fixing structure 100 is fixed to more than three vertebras.

Referring to FIG. 10A, the third joint element 330 further a receiving cavity 333 and a block portion (not illustrated) which is similar to the receiving cavity 323 and the block portion 324 respectively. The second joint element 320 is flexibly connected to the third joint element 330 through the flange 322 of the second joint element 320 being movably connected to the block portion of the third joint element 330.

Referring to FIG. 10A, the flexible spine fixing structure 300 further comprises a soft element 370 disposed within the first through hole 315 of the first joint element 310. The soft element 370 has a through hole 371 and the first flexible element 340 passes through the through hole 371 of the soft element 370. Due the soft element 370 possessing the soft property, the first flexible element 340 is movably disposed to the first joint element 310. In addition, another soft elements 370 are disposed within the second through hole 325 and the third through hole 335 respectively. The second flexible element 350 and the third flexible element 360 pass through the second through hole 325 and the third through hole 335 respectively. In another embodiment, the soft element 370 can be omitted.

In addition, the soft element 370 is made of a polymer, a flexible material, an elastic material or a combination thereof. For example, the polymer may be realized by polyether ether ketone (PEEK), polytetrafluoroethylene (PTFE, that is Teflon), polyethylene terephthalate (PET) or polysiloxanes.

Referring to FIG. 10A, the first joint element has two wire through hole 316 passing through the first joint element 310, such that a wire (not illustrated) may pass through the wire through holes 316 to fix to a first vertebra 102. In addition, the second joint element 320 has four wire through holes 316, and the third joint element 330 has two wire through holes 316.

Fourth Embodiment

Figure 11A:
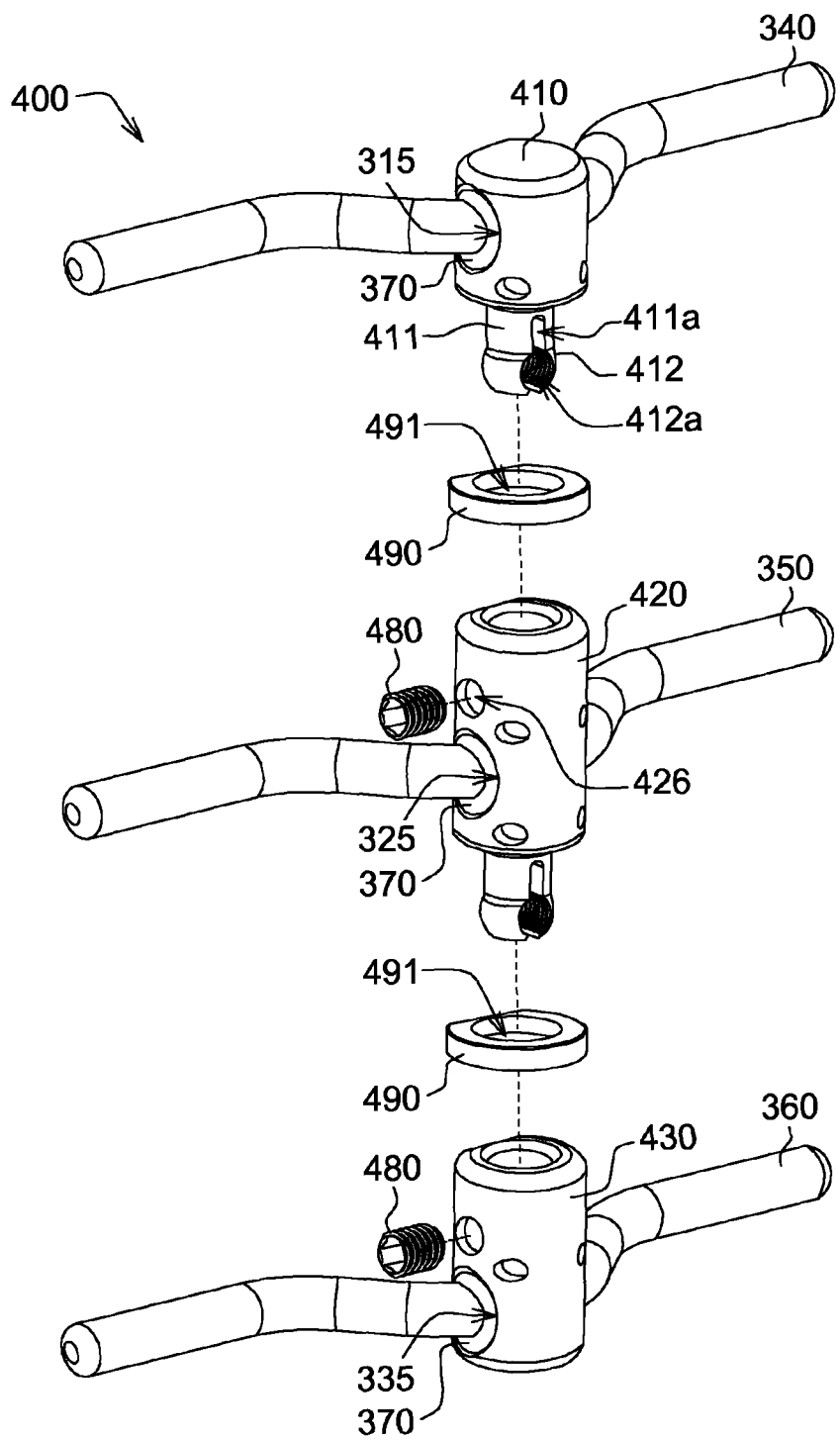
FIG. 11A is a explode diagram of the flexible spine fixing structure configured on vertebras according to a fourth embodiment of the disclosure.

Referring to FIG. 11A, a explode diagram of the flexible spine fixing structure configured on vertebras according to a fourth embodiment of the disclosure is shown. The flexible spine fixing structure 400 comprises a first joint element 410, a second joint element 420, a third joint element 430, a first flexible element 340, a second flexible element 350 and a third flexible element 360. The first joint element 410 has a first through hole 315, and the first flexible element 340 passes through the first through hole 315 of the first joint element 410. The second joint element 420 has a second through hole 325, and the second flexible element 350 passes through the second through hole 325 of the second joint element 420. The third joint element 430 has a third through hole 335, and the third flexible element 360 passing through the third through hole 335 of the third joint element 330. In another embodiment, the flexible spine fixing structure 400 may omit the third joint element 430.

The first joint element 410 comprises a protrusion 411 and a flange 412 disposed on the protrusion 411, wherein an outer diameter of the flange 412 is larger an outer diameter of the protrusion 411. In present embodiment, the flange 412 of the first joint element 410 has a recess 412a, and the second joint element 420 has a fixing hole 426. Due to the recess 412a reducing the stiffness of the flange 412, the flange 412 is deformable such that the flange 412 may easily enter the receiving cavity 423 (FIG. 11B) of the second joint element 420 after a force applied to the first joint element 410. In another embodiment, the recess 412a can be omitted.

The flexible spine fixing structure 400 further comprises a first connecting element 480. The first connecting element 480 may pass through the fixing hole 426 of the second joint element 420 and the recess 412a of the flange 412 for connecting the first joint element 410 and the second joint element 420. In present embodiment, an inner side wall of the fixing hole 426 has a female thread through which the first connecting element 480 passes to connect the second joint element 420 and the flange 412. In another embodiment, inner side wall of the fixing hole 426 may be a side wall without the female thread.

In present embodiment, the fixing hole 426 may fully penetrates through the second joint element 420. In another embodiment, the fixing hole 426 may penetrates through a portion of the second joint element 420a.

Referring to FIG. 11A, the protrusion 411 has a recess 411a connected to the recess 412a of the flange 412. Due to the recess 411a and 412a reducing the stiffness of the protrusion 411 and the flange 412, the protrusion 411 and the flange 412 are deformable, such that the flange 412 may further easily enter the receiving cavity 423 (FIG. 11B) of the second joint element 420 after a force applied to the first joint element 410. In another embodiment, the recess 411a can be omitted.

In addition, the flange 412 has a female thread disposed to the recess 412a of the flange 412, and the first connecting element 480 has a pin thread corresponding to the female thread of the flange 412, such that the flange 412 and the second joint element 420 do not separated from each other through the first connecting element 480 being fixing the flange 412 and second joint element 420.

The length of the first connecting element 480 (such as set screw) is shorter than the inner diameter of the receiving cavity 423 (FIG. 11B), such that the whole first connecting element 480 may be received within the receiving cavity 423 after the first connecting element 480 is connected to the flange 412. In addition, before the first connecting element 480 is connected to the flange 412, the first joint element 410 may rotate to let the recess 412a of the flange 412 to face fixing hole 426, and then the first connecting element 480 may enter the recess 412a of the flange 412 for connecting to the flange 412.

Figure 11B:
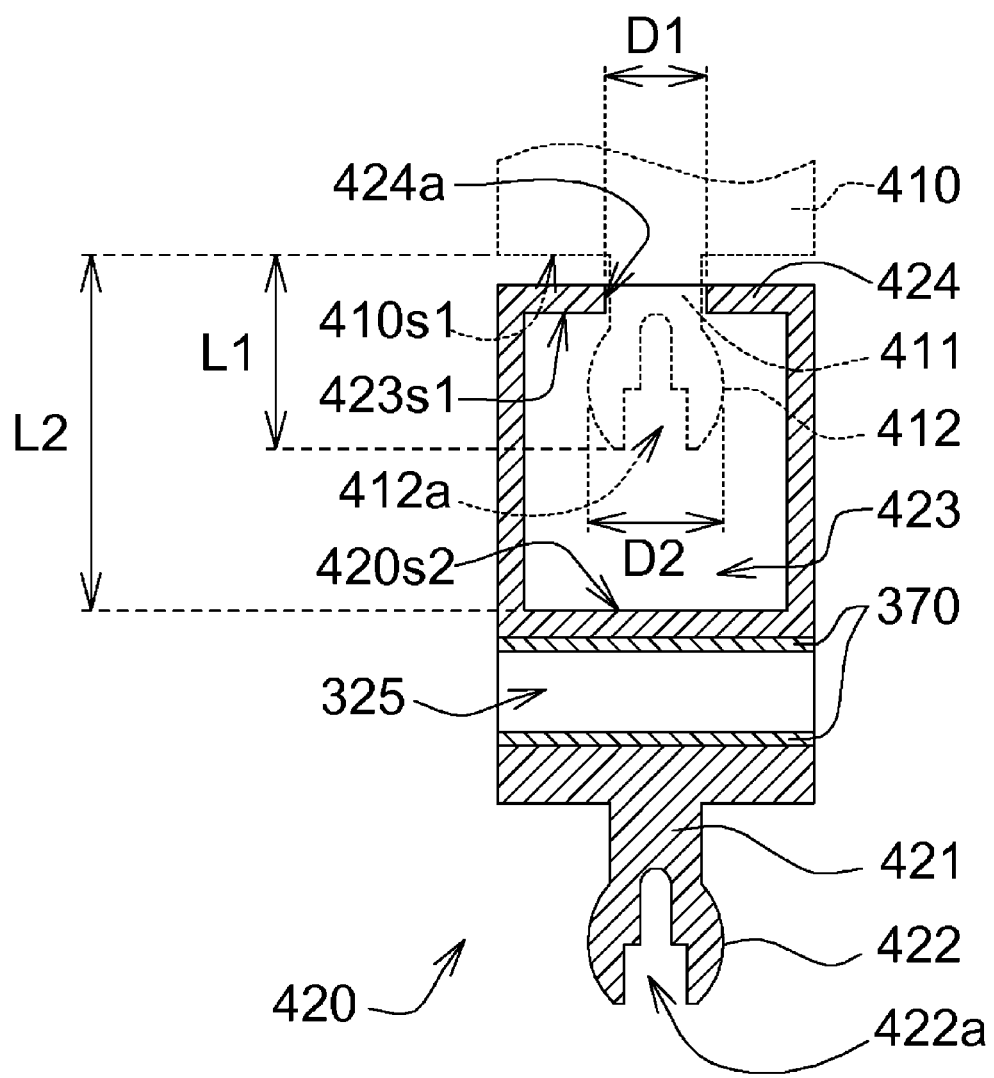
FIG. 11B is a cross-section view of the second joint element of FIG. 11A.

Referring to FIGS. 11A and 11B, and FIG. 11B is a cross-section view of the second joint element of FIG. 11A. The second joint element 420 comprises a receiving cavity 423 and a block portion 424 disposed in the receiving cavity 423, wherein the block portion is smaller than the flange 412, and the first joint element 410 is flexibly connected to the second joint element 420 through the flange 412 is movably disposed within the receiving cavity 423. In present embodiment, the block portion 424 has an aperture 424a and an inner diameter D1 of the aperture 424a is smaller than an outer diameter D2 of the flange 412, such that the first joint element 410 and the second joint element 420 do not separate from each other. In addition, the inner diameter D1 may be smaller than the length of the first connecting element 480.

In addition, the length L1 from a lower surface 410s1 of the first joint element 410 to a end of the flange 412 is shorter than the length L2 from the lower surface 410s of the first joint element 410 to a lower surface 420s2 of the second joint element 420, such that the flange 412 is movably disposed within the receiving cavity 423. The length of the protrusion 411 is longer than the distance from an upper surface 423s1 of the receiving cavity 423 to the lower surface 410s1 of the first joint element 410, such that the protrusion 411 is movably disposed to the aperture 424a.

In addition, the second joint element 420 further comprises a protrusion 421 and a flange 422 which are similar to the protrusion 411 and the flange 412 respectively. The second joint element 420 is connected to third joint element 430 through the flange 422.

The flexible spine fixing structure 400 further comprises a buffer 490 disposed between the first joint element 410 and the second joint element 420. Due to the buffer 490, the first joint element 410 is movable with respect to the second joint element 420. In addition, another buffer 490 is disposed between the second joint element 420 and the third joint element 430. Due to another buffer 490, the second joint element 420 is movable with respect to the third joint element 430. In addition, the buffer 490 may be applied to the flexible spine fixing structure 300. In another embodiment, buffer 490 can be omitted.

The buffer 490 has a through hole 491, and the protrusion 411 and flange 412 of the first joint element 410 may pass through the through hole 491 of the buffer 490 to enter receiving cavity 423. In addition, the buffer 490 is made of a polymer, a flexible material, an elastic material or a combination thereof, wherein the polymer may be realized by polyether ether ketone (PEEK), polytetrafluoroethylene (PTFE, that is Teflon), polyethylene terephthalate (PET) or polysiloxanes.

Fifth Embodiment

Figure 12A:
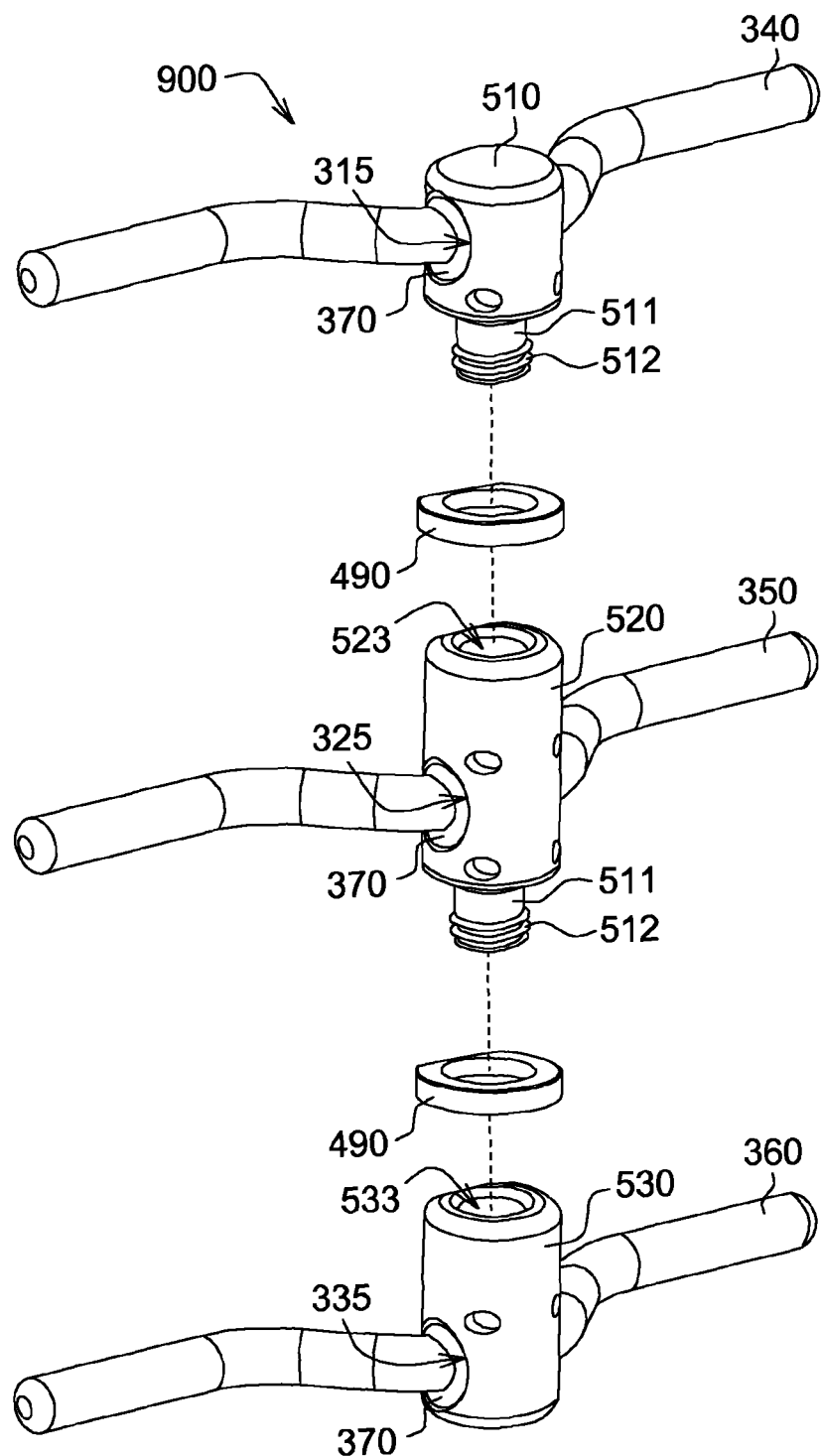
FIG. 12A is a explode diagram of the flexible spine fixing structure configured on vertebras according to a fifth embodiment of the disclosure.

Referring to FIG. 12A, a explode diagram of the flexible spine fixing structure configured on vertebras according to a fifth embodiment of the disclosure is shown. The flexible spine fixing structure 500 comprises a first joint element 510, a second joint element 520, a third joint element 530, a first flexible element 340, a second flexible element 350 and a third flexible element 360. The first joint element 510 has a first through hole 315, and the first flexible element 340 passes through the first through hole 315 of the first joint element 510. The second joint element 520 has a second through hole 325, and the second flexible element 350 passes through the second through hole 325 of the second joint element 520. The third joint element 530 has a third through hole 335, and the third flexible element 360 passing through the third through hole 335 of the third joint element 540. In another embodiment, the flexible spine fixing structure 500 may omit one of the first joint element 510, the second joint element 520 and the third joint element 530.

Figure 12B:
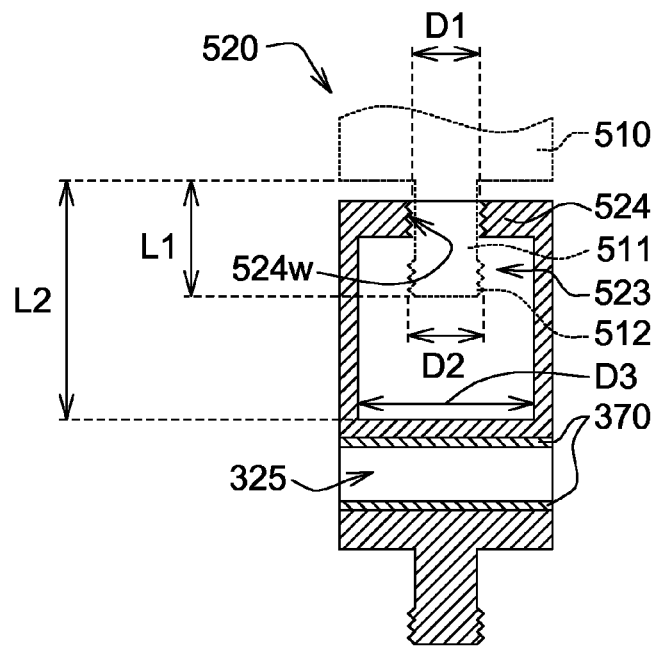
FIG. 12B is a cross-section view of the second joint element of FIG. 12A.

Referring to FIGS. 12A and 12B, FIG. 12B is a cross-section view of the second joint element of FIG. 12A. The first joint element 510 comprises a protrusion 511 and a flange 512 disposed on the protrusion 511, wherein an outer diameter D2 of the flange 512 is larger an outer diameter of the protrusion 511. In present embodiment, the flange 512 of the first joint element 510 is a pin thread which surrounds the protrusion 511. The first joint element 510 is connected to second joint element 520 through the flange 512.

Referring to FIG. 12B, the second joint element 520 comprises a receiving cavity 523 and a block portion 524 disposed in the receiving cavity 523, wherein the block portion 524 is smaller than the flange 512 of the first joint element 510, and the first joint element 510 is flexibly connected to the second joint element 520 through the flange 512 being movably disposed within the receiving cavity 523. In present embodiment, the flange 512 is a pin thread, the block portion 524 has an inner side wall 524w having an inner diameter D1, the inner diameter D1 of the inner side wall 524w is smaller than the outer diameter D2 of the flange 512, and the inner side wall 524w is a female thread. In addition, the inner diameter D1 of the inner side wall 524w is small than an inner diameter D3 of the receiving cavity 523.

Referring to FIG. 12A, the third joint element 530 further comprises a receiving cavity 533 and a block portion (not illustrated) which are similar to the receiving cavity 523 and the block portion 524 respectively. The second joint element 520 is flexibly connected to the third joint element 530 through the flange 522 of the second joint element 520 being movably connected to the block portion of the third joint element 530.

Figure 13:
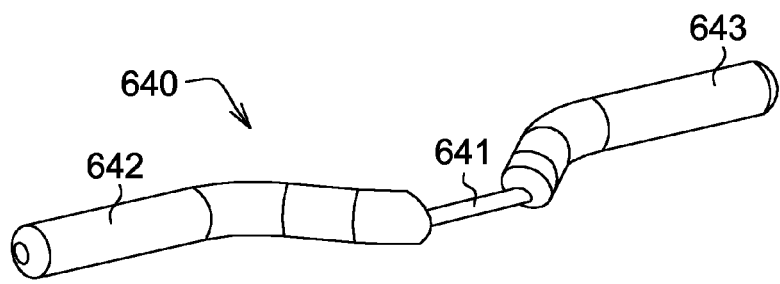
FIG. 13 is a schematic diagram of first flexible element according to another embodiment of the disclosure.

Referring to FIG. 13, a schematic diagram of first flexible element according to another embodiment of the disclosure is shown. The first flexible element 640 comprises a thin portion 641, a first thick portion 642 and a second thick portion 643, and the thin portion 641 connects the first thick portion 642 and the second thick portion 643. The thin portion 641 may disposed to the first through hole 315 of the first joint element 310, 410 or 510. Due to the thin portion 641, first flexible element 640 is deformable. In one embodiment, the first thick portion 642, the second thick portion 643 and the thin portion 641 may be made of the same material or several different materials. In another embodiment, the thin portion 641 may be a metal wire containing titanium such as pure titanium or titanium alloy. The thin portion 641 and the first thick portion 642 may be made of a material similar to the first flexible element 340.

In one embodiment, take the first flexible element 340 for example, a metal wire (not illustrated) containing titanium such as pure titanium or titanium alloy may be embedded within the first flexible element 340. Similarly, a metal wire (not illustrated) may be embedded within the second flexible element 350, and a metal wire (not illustrated) may be embedded within the third flexible element 360.

In another embodiment, take the first joint element 310 and the first flexible element 340 for example, the first joint element 310 and the first flexible element 340 are integrated into one piece. For example, the first joint element 310 and the first flexible element 340 are made by the same manufacturing process (such as Injection or double Injection using the same material or different material. Similarly, the second joint element 320 and the second flexible element 350 may be integrated into one piece, and the third joint element 330 and the third flexible element 360 may be integrated into one piece.

Figure 14:
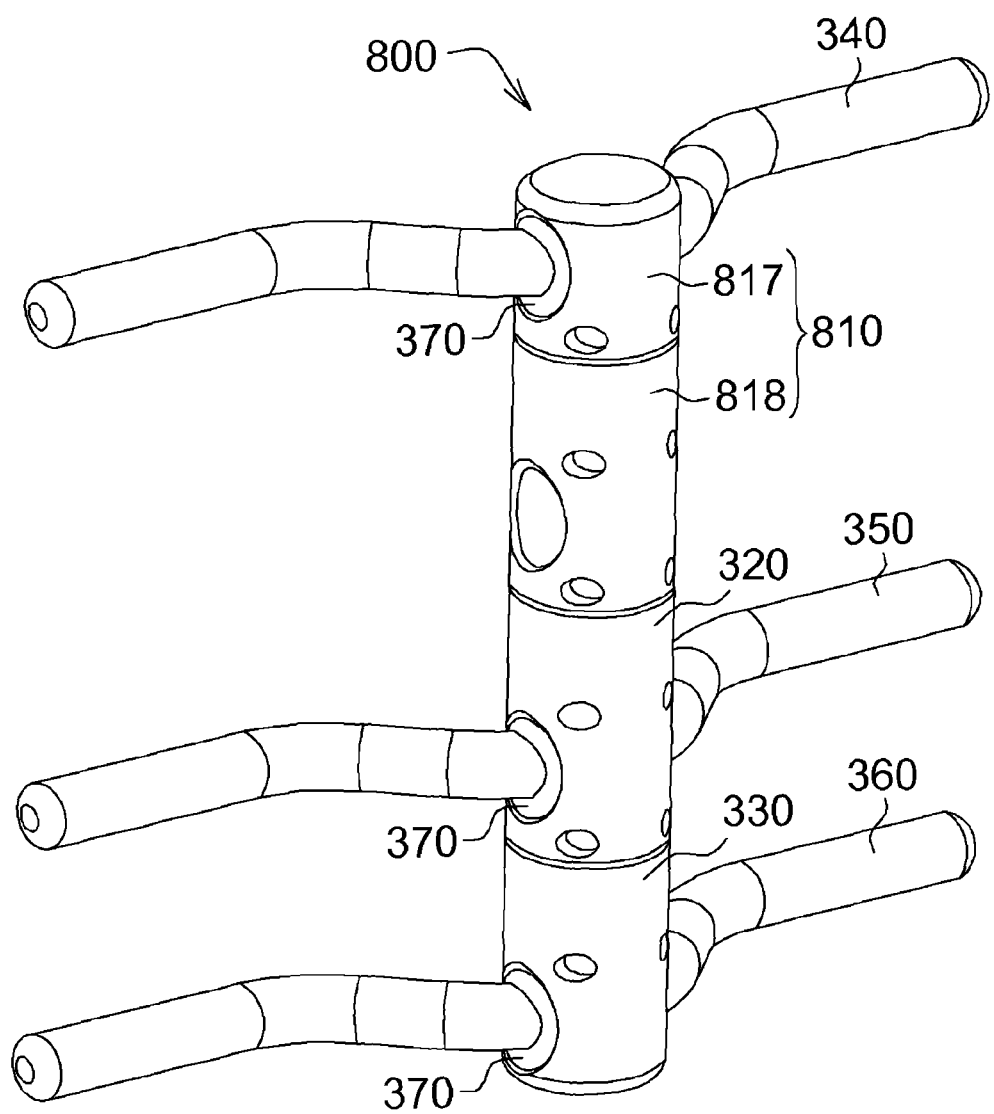
FIG. 14 is a schematic diagram of the flexible spine fixing structure configured on vertebras according to another embodiment of the disclosure.

Referring to FIG. 14, a schematic diagram of the flexible spine fixing structure configured on vertebras according to another embodiment of the disclosure is shown.

The first joint element 810 of the flexible spine fixing structure 800 comprises a first body 817 and an extending joint element 818, wherein the extending joint element 818 detachably connects the first body 817 and the second joint element 320. The first flexible element 340 passes through the first body 817, and the protrusion 311 (illustrated in FIG. 10A) and the flange 312 (illustrated in FIG. 10A) are disposed on the extending joint element 818.

In present embodiment, there is no any flexible element (such as the first flexible element 340, the second flexible element 350 or the third flexible element 360) passes through the extending joint element 818. In addition, since the extending joint element 818 may correspond to one vertebra, the first flexible element 340 and the second flexible element 350 may be fixed to two vertebras which are not adjacent to each other.

In present embodiment, the structure of the first body 817 may be similar to the structure of the first joint element 310 (FIG. 10A), such that the first body 817 detachably connects to the extending joint element 818. In addition, the structure of the extending joint element 818 may be similar to the structure of the second joint element 320 of FIG. 10A, such that the extending joint element 818 detachably connects to the second joint element 320 of FIG. 14.

In another embodiment, the first joint element 410 (FIG. 11A) may comprise a first body and an extending joint element which are similar to the first body 817 and the extending joint element 818 respectively. In another embodiment, the first joint element 510 (FIG. 12A) may comprise a first body and an extending joint element which are similar to the first body 817 and the extending joint element 818 respectively.

Figure 15:
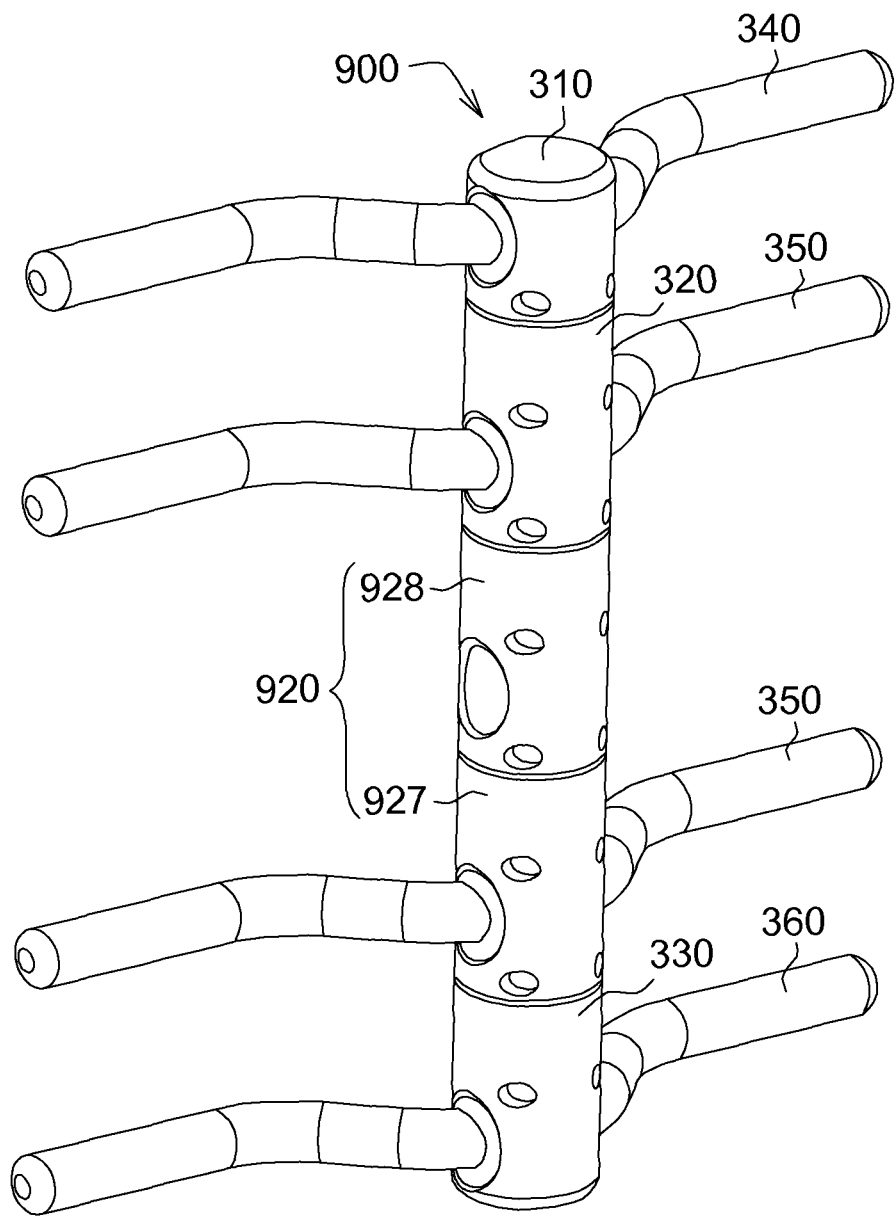
FIG. 15 is a schematic diagram of the flexible spine fixing structure configured on vertebras according to another embodiment of the disclosure.

Referring to FIG. 15, a schematic diagram of the flexible spine fixing structure configured on vertebras according to another embodiment of the disclosure is shown.

The second joint element 920 of the flexible spine fixing structure 900 comprises a second body 927 and an extending joint element 928, wherein the extending joint element 928 detachably connects the second body 927 and the second joint element 320. The second flexible element 350 passes through the second body 927, and the receiving cavity 323 of FIG. 10B and the block portion 324 of FIG. 10B are disposed on the extending joint element 928.

In present embodiment, there is no any flexible element (such as the first flexible element 340, the second flexible element 350 or the third flexible element 360) passes through the extending joint element 928. In addition, since the extending joint element 928 may correspond to one vertebra, two second flexible element 350 of FIG. 15 may be fixed to two vertebras respectively which are not adjacent to each other.

In present embodiment, the structure of the second body 927 may be similar to the structure of the second joint element 320 (FIG. 10A), such that the second body 927 detachably connects to the third joint element 330 of FIG. 15. In addition, the structure of the extending joint element 928 may be similar to the structure of the second joint element 320 (FIG. 10A), such that the extending joint element 928 detachably connects to the second joint element 320 of FIG. 15.

In another embodiment, the second joint element 420 (FIG. 11A) may comprise second body and an extending joint element which are similar to the second body 927 and the extending joint element 928 respectively. In another embodiment, the second joint element 520 (FIG. 12A) may comprise second body and an extending joint element which are similar to the second body 927 and the extending joint element 928 respectively.

The flexible spine fixing structure disclosed by the above embodiments includes a first flexible element connected to a second flexible element such that the whole spine fixing structure has flexibility. After the flexible spine fixing structure is fixed to the vertebras, the fixed vertebras can still move and thus the patient can still bend his/her body forwards or backwards or turn his/her body left or right to have a higher mobility and lower discomfort after surgery and the spine degeneration can be avoided.

It will be apparent to those skilled in the art that various modifications and variations can be made to the disclosed embodiments. It is intended that the specification and examples be considered as exemplary only, with a true scope of the disclosure being indicated by the following claims and their equivalents.

What is claimed is:

1. A flexible spine fixing structure for fixing to a first vertebra and a second vertebra, comprising:
   a first joint element comprising a first protrusion and a first flange disposed on the first protrusion, wherein the first flange is a pin thread and only disposed on the end of the first protrusion;
   a second joint element comprising a receiving cavity, a block portion disposed in the receiving cavity, a second protrusion and a second flange, wherein the block portion has an aperture, the outer diameter of the first flange is larger than the inner diameter of the aperture but smaller than the inner diameter of the receiving cavity, only the inner side wall of the aperture is a female thread, and the first joint element is flexibly connected to the second joint element through the first flange being movably disposed within the receiving cavity;
   a first flexible element passing through the first joint element for fixing to the first vertebra; and
   a second flexible element passing through the second joint element for fixing to the second vertebra.

2. The flexible spine fixing structure according to claim 1, wherein an outer diameter of the first flange is larger than an outer diameter of the first protrusion.

3. The flexible spine fixing structure according to claim 1, wherein the block portion of the second joint element is the female thread corresponding to the pin thread.

4. The flexible spine fixing structure according to claim 1, further comprises:
   a buffer disposed between the first joint element and the second joint element.

5. The flexible spine fixing structure according to claim 1, wherein the first joint element has a first through hole, and the first flexible element is disposed in the first joint element by passing through the first through hole, and the second joint element has a second through hole and the second flexible element is disposed in the second joint element by passing through the second through hole.

6. The flexible spine fixing structure according to claim 5, further comprises:

a soft element disposed to the first joint element, wherein the soft element has a through hole and the first flexible element passes through the through hole of the soft element.

7. The flexible spine fixing structure according to claim 6, wherein the soft element is made of a polymer.

8. The flexible spine fixing structure according to claim 1, further comprises:
a third joint element comprising a receiving cavity and a block portion disposed in the receiving cavity of the third joint element, wherein an inner diameter of the block portion of the third joint element is smaller than an outer diameter of the second flange of second joint element, and the second joint element is flexibly connected to the third joint element through the second flange of the second joint element being movably disposed within the receiving cavity of the third joint element.

9. The flexible spine fixing structure according to claim 1, wherein the first flexible element comprises a thin portion, a first thick portion and a second thick portion, and the thin portion connects the first thick portion and the second thick portion.

10. The flexible spine fixing structure according to claim 1, wherein at least one of the first flexible element and of the second flexible element is made of a metal or a polymer or combination thereof.

11. The flexible spine fixing structure according to claim 1, wherein the first joint element has a plurality of wire through holes, such that a wire passes through the wire through holes to fix to the first vertebra.

12. The flexible spine fixing structure according to claim 1, wherein the first joint element further comprises:
a first body, wherein the first flexible element passes through the first body; and
an extending joint element corresponding to another vertebra, wherein the extending joint element detachably connects the first body and the second joint element, and the first protrusion of the first joint element and the first flange of the first joint element are disposed on the extending joint element.

13. The flexible spine fixing structure according to claim 1, wherein the second joint element further comprises:
a second body, wherein the second flexible element passes through the second body; and
an extending joint element corresponding to another vertebra, wherein the extending joint element detachably connects the second body and the first joint element, and the receiving cavity and the block portion are disposed on the extending joint element.

* * * * *